US00PP09519P

United States Patent [19]

Egger et al.

[11] Patent Number: Plant 9,519

[45] Date of Patent: Apr. 23, 1996

[54] ASIATIC HYBRID LILY PLANT NAMED 'CEB FUZZY'

[76] Inventors: Donald L. Egger, 7115 SW. Frog Pond La., Wilsonville, Oreg. 97070; Teresa Pankiewicz-Leap, 5854 SE. Flavel Dr., Portland, Oreg. 97206

[21] Appl. No.: 398,341

[22] Filed: Mar. 3, 1995

[51] Int. Cl.[6] ..... A01H 5/00

[52] U.S. Cl. ..... Plt./87.4

[58] Field of Search ..... Plt./87.4

*Primary Examiner*—James R. Feyrer

*Attorney, Agent, or Firm*—Klarquist Sparkman Campbell Leigh & Whinston

[57] ABSTRACT

A new and distinct Asiatic lily hybrid named 'Ceb Fuzzy' characterized by upright, pink flowers with numerous spots, dark pollen and striking buds heavily covered with white hairs.

1 Drawing Sheet

BACKGROUND OF THE INVENTION

The present invention comprises a new and distinct cultivar of Lily Hybrid, referred to commercially as an upright Asiatic Lily Hybrid, referred to by the cultivar name 'CEB Fuzzy'.

This invention is the product of a controlled breeding program in Aurora, Oreg. The seed parent was an unnamed seedling identified as 94-81. This seed parent has not been released and was kept proprietary. The pollen parent was A-107-82, another proprietary non-released plant.

This invention has not been observed under all possible environmental conditions. The phenotype may vary significantly with variations in environment such as tmperature, light intensity and day length without, however, any variation in genotype. The following traits have been repeatedly observed and are determined to be the basic characteristics of this invention which in combination distinguish this lily as a new and distinct cultivar: 1) pink flowers with dark spots and an ivory blush; 2) beautiful large, white villous, dark pink buds extending the show time of the plant as the hairs are striking even on green buds; 3) very dark purple pollen making a nice contrast with the tepals; 4) very early bloom time; 5) white villous hairs on buds, stems and leaves; 6) dark stems. Bulbs of this plant may be precooled and forced out of season for uniform cut flower production. In addition, this new lily shows good disease tolerance.

To the inventor's knowledge, there are no other Asiatic lily hybrids with this color flower suitable for cut flower forcing on the market.

Asexual reproduction of this new variety has been initially and subsequently accomplished at Cebeco Lillies, Inc. in Aurora, Oreg. by scaling and tissue culture. The resulting plants have shown that the above-mentioned unique features are stable and reproduce true to type in each successive propagation.

Figure 2:
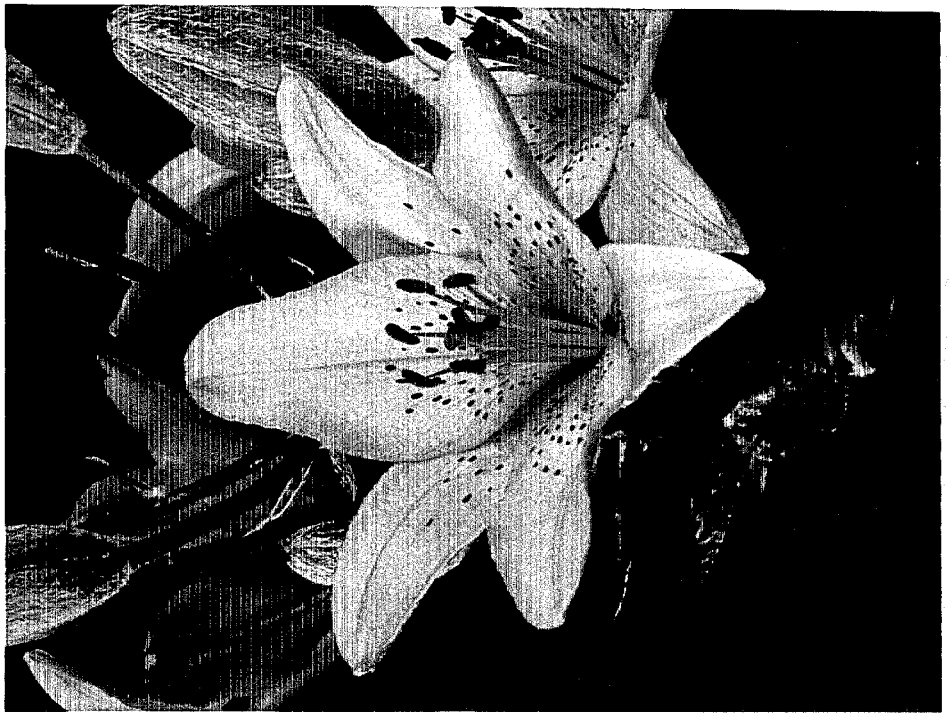
FIG. 2 is a close-up photograph which illustrates in greater detail a single flower of the new plant.
Figure 1:
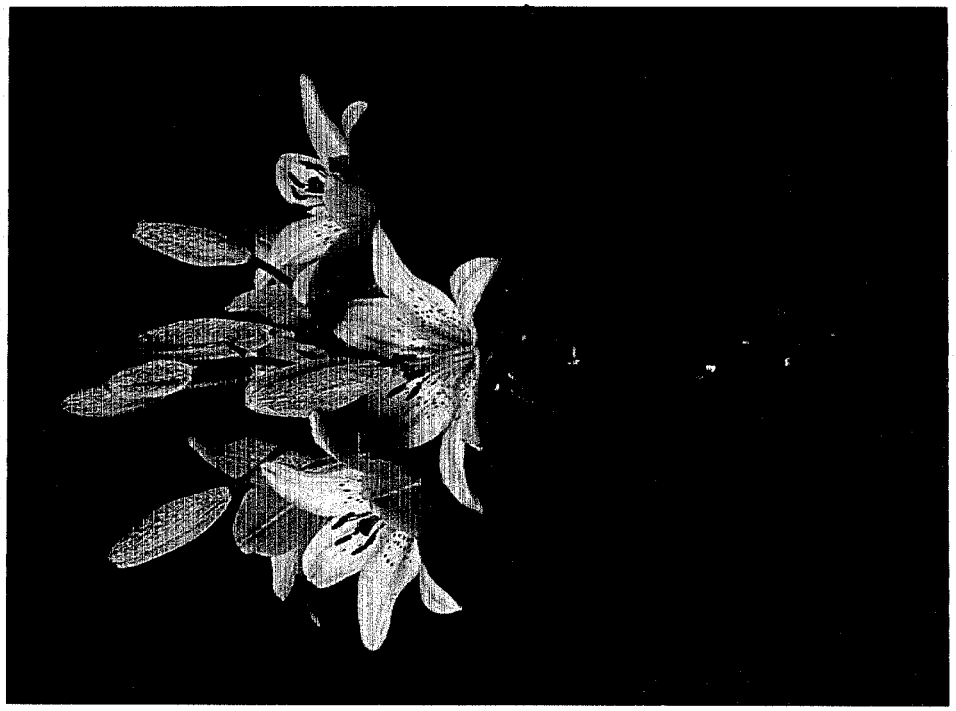
FIG. 1 is a photograph showing the 'Ceb Fuzzy' lily.

The photographs of the drawing were taken in July 1994 in a studio and illustrate the typical flower and foliage form, with color being as true as is reasonably possible in this type of color photograph.

DETAILED DESCRIPTION

The following is a detailed description of the invention based on plants produced under commercial practices in the Cebeco Lilies, Inc. fields in Aurora, Oreg. in July 1994. Color references are made to The Royal Horticultural Society Colour Chart (R.H.S.), except where the context indicates a term having its ordinary dictionary meaning.

THE PLANT

Origin: Seedling.

Parentage:

*Seed parent.*—94-81.

*Pollen parent.*—A-107-82.

Commercial classification: Hybrid asiatic Lily, garden type.

Classification: Division I-A, Upright Asiatic Hybrid Lily, according to the Horticultural Classification of Lilies by The Royal Horticultural Society of London.

Form: Single erect stem bearing terminal cluster of flowers.

Height: About 87 cm. from the top of the soil to the top of the flowers from bulbs of 12–14 cm. in circumference.

Stem color: Dark purple. Greyed-Purple Group 185A.

Growth habit: Vigorous, upright and rigid.

Foliage:

*Arrangement.*—Spiral.

*Leaf size.*—To about 9 cm. long.

*Leaf shape.*—Lanceolate.

*Texture.*—Leathery.

*Aspect.*—Glossy when mature with sparse villous hairs on margins and dense hairs at leaf axils. When young, the leaves have white villous hairs on the surface, margins and densely on the backs and in the axils.

*Color.*—Medium green on both sides. Closest to Yellow-Green Group 147B.

Bulbs:

*Size.*—Variable, ranging to about 12–14 cm. in circumference as used commercially.

*Color.*—White.

THE BUD

Size: Large, to about 8 cm. long and 25 mm. wide just prior to opening.

Shape: Ovoid with an obtuse tip.

Rate of opening: The mature bud opens slowly in response to light.

Color: Dark rose, Red-Purple Group 59C-D, and covered with white villous hairs.

THE FLOWER

Blooming habit: Annually, once and early season.

Days to bloom: Flowers approximately 64 days after spring greenhouse planting under typical commercial flower forcing conditions of 15° Celsius night time temperatures.

Inflorescence size: About 26 cm. high and 26 cm. wide when there are eleven flowers present.

Flower size: Medium large.

*Diameter.*—About 14 cm.

*Depth.*—About 5 cm.

Borne: In an umbel or modified raceme of 6 flowers from bulbs 12 cm. in circumference.

Shape: When the flower first opens it is bowl-shaped. Later, the shape flattens out and the tepals reflex slightly at the tips.

Tepalage:

*Number.*—Six.

Arrangement.—Imbricated.

*Shape.*—Ovate.

*Texture.*—Spongy, waxy.

*Aspect.*—Dull gloss. Bottomside with white villous hairs on veins.

*Size.*—Length: About 8.3 cm. Width: Inner tepals—about 40 mm. Outer tepals—about 28 mm. Depth of Imbrication: About 8 mm.

*Nectary.*—About 2.5 cm. long; warm pink; glandular pubescent; channels together.

*Projections.*—Present on either side of the nectary, the upper ones terminating in spots.

*Spots.*—On bottom ⅔ of tepals, linear ovoid in shape, occasionally running up midrib. Greyed-Purple Group 187A.

*Blush.*—Above the nectary, ivory.

*Color.*—Topside: Warm pink. Red Group 54A-B. Lightens to Red Group 54C with age.

*Bottomside: Inner tepals: Red Group* 54A. Outer tepals: Red-Purple Group 59D.

*Discoloration.*—A Shade lighter with age.

*Fragrance.*—None.

Pedicel:

*Length.*—About 9 cm.

*Color.*—Yellow green overlayed with maroon spots, Greyed-Purple Group 185A. The spots are heavist where the sun reaches the pedicel.

*Orientation.*—Ascending upwardly in a curve to about 45° from the horizontal.

THE REPRODUCTIVE ORGANS

Stamens:

*Number.*—Six, typical of the genus Lilium.

*Anthers before dehiscence.*—About 16 mm. Color: Dark Purple Brown. Closest to Greyed-Purple Group 187A.

*Filaments.*—Length: About 5.2 cm. Color: Purple Pink, Red-Purple Group 59A near top to 59B to 59C to white at the base.

*Pollen.*—Color: Appears Dark Purple Brown. Greyed-Orange Group 175A.

Pistil:

*Number.*—One.

*Style.*—Length: About 37 mm. Color: Rose, Red-Purple Group 60B on top to yellow green at base.

*Stigma.*—Color: Brown. Greyed-Orange Group 177A.

THE FRUIT

Fertility: The fruit is fertile.

Shape: Ovoid.

Color at Maturity: Soft Brown.

I claim:

1. A new and distinct cultivar of Asiatic hybrid lily plant substantially as herein shown and described.

* * * * *